United States Patent [19]

Siegal

[11] Patent Number: 5,316,012
[45] Date of Patent: May 31, 1994

[54] DEVICE FOR TESTING PIN PRICK SENSATION

[76] Inventor: Tzony Siegal, Gelber St. 16, Jerusalem, Israel

[21] Appl. No.: 15,905
[22] Filed: Feb. 10, 1993
[51] Int. Cl.⁵ .............................................. A61B 19/00
[52] U.S. Cl. .............................................. 128/744
[58] Field of Search ........................ 128/740, 744, 774

[56] References Cited

U.S. PATENT DOCUMENTS

| | | | |
|---|---|---|---|
| 3,074,395 | 1/1963 | Kevorkian | 128/744 |
| 3,344,781 | 10/1967 | Allen | 128/744 |
| 3,515,125 | 6/1970 | Ruskin | 128/744 |
| 4,823,806 | 4/1989 | Bajada | 128/744 |

FOREIGN PATENT DOCUMENTS 1066536 1/1984 U.S.S.R. ................... 128/744

*Primary Examiner*—Max Hindenburg
*Attorney, Agent, or Firm*—Michael D. Bednarek

[57] ABSTRACT

The present invention relates to a device for testing pin prick sensation comprising a handle, at the upper end of which are located movable holding means, actuating means causing the holding means to move; and a rotatable wheel bearing pins; the holding means having the size and dimensions corresponding to those of the wheel acting as an axis for the rotation of the wheel and enabling both grasping and rotating of the wheel. The holding means may consist of two parts, being (a) moving mans moving towards (b) fixed means. The actuating means may be operated by a spring.

4 Claims, 2 Drawing Sheets

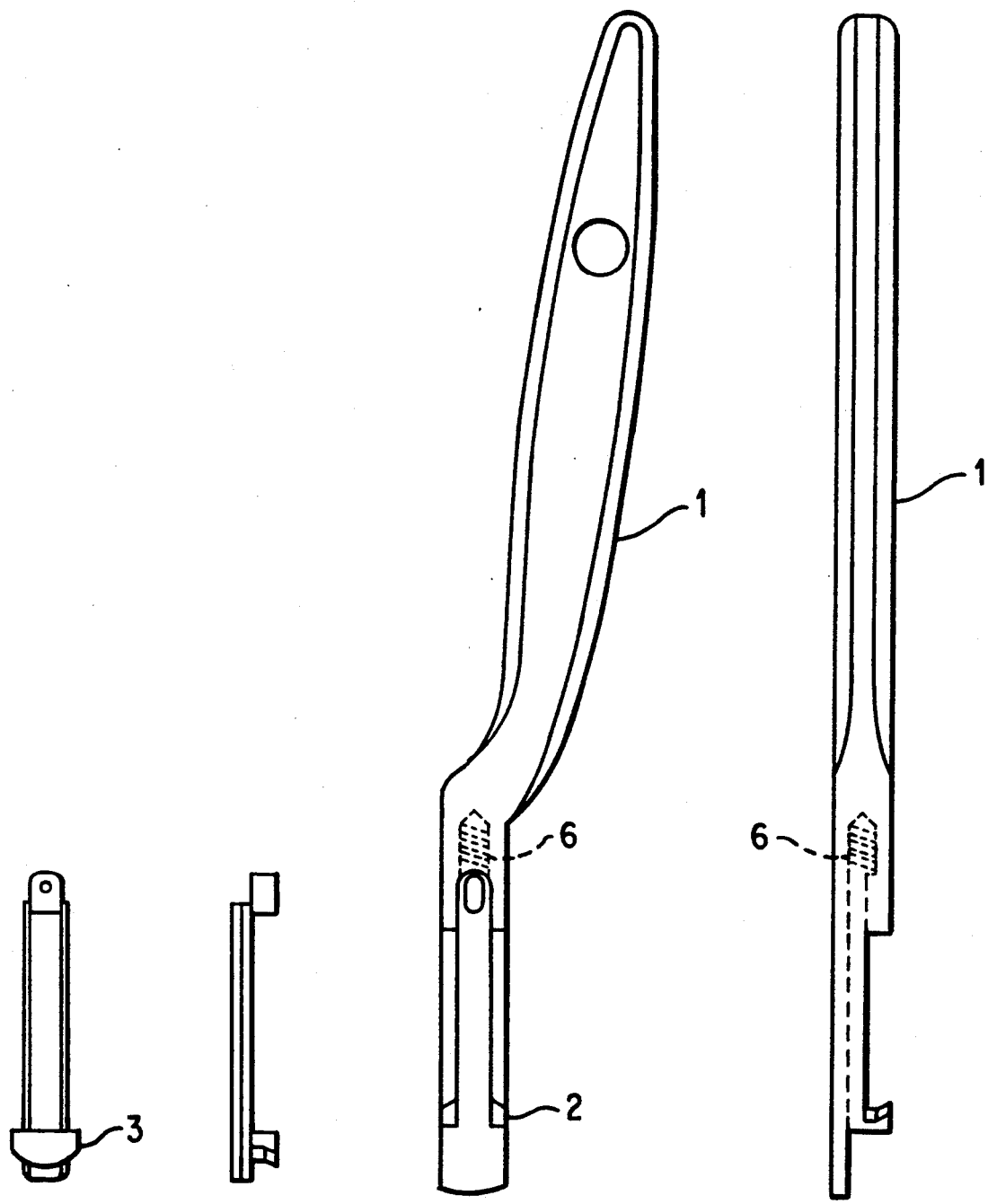

DEVICE FOR TESTING PIN PRICK SENSATION

The present invention relates to a device for testing pin prick sensation.

The AIDS world epidemic assuming the current frightening proportions has brought about an acute interest in ways and means to limit its spread.

Most neurologists, neurosurgeons and orthopoedic surgeons in the U.S.A. have used fixed devices for testing pin prick sensation, namely metallic pins, some of them contained within the reflex hammer, or the well known Wartenberg pin wheel. These testing modalities have fallen in disrepute and have been severely condemned in some recent publications for their potential in contaminating unsuspecting victims with possibly lethal transmissible viral diseases, like hepatitis and AIDS.

In many hospitals and clinics pin prick sensation is tested by disposable needles or by wooden tooth picks. However, these may cause unnecessary skin penetration and scratches besides being non-exact (amount of pressure while testing may change from prick to prick) and unrefined.

It has therefore been desirable to design a device which overcomes the above disadvantages, i.e. avoids the possible transfer of any virus, bacteria, etc. from one person to another, and simultaneously ensures appropriate testing. Said device should be easy to use and be relatively cheap to manufacture.

The present invention thus consists in a device for testing pin prick sensation comprising a handle, at the upper end of which are located movable holding means, actuating means causing the holding means to move; and a rotatable wheel bearing pins; the holding means having the size and dimensions corresponding to those of the wheel acting as an axis for rotation of the wheel and enabling both grasping and rotating of the wheel.

It is readily understood that the moment the holding means are moved, hey will no longer hold the wheel which is discarded. A new wheel may be attached by causing the holding means to return to its original position. The movable holding means may consist of two parts, namely (a) movable means moving to (b) fixed means.

The radius of the wheel and the number of pins are determined by the customers and are not a critical feature of the device. The same applies to the form and length of the handle. The handle and the wheel may be made from any suitable material, metal or rigid plastic.

The actuating means are preferably operated by a spring. In this version, the movable holding means are pushed against the centre of the pin wheel causing it to settle with a snap on the holding means. However, also manual means may be used.

The device according to the present invention functions very much like the Wartenberg pin wheel, namely it allows the examiner a steady pressure while the pins of the rotating wheel are touching but not penetrating the patient's skin. The pin wheel is discarded following each and every test and a new wheel installed in the handle, which is permanent. The discardable pin wheel is easily snapped on the handle and off it with a no-touch technique.

The present invention will now be illustrated with reference to the accompanying drawings without being limited by them. Identical parts appearing in various Figures are referenced by the same numeral.

In said drawings:

FIGS. 3 and 3A show top and side views, respectively, of the part holding the wheel; and FIGS. 4 and 4A show top and side views, respectively, of a longitudinal cross-section of the device shown in FIG. 1.

Figure 1:
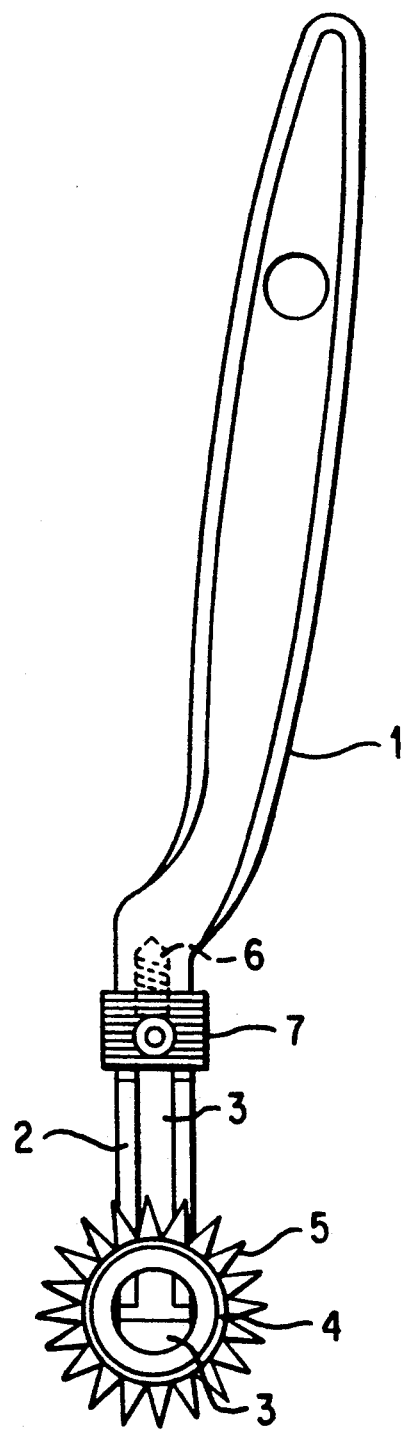
FIG. 1 shows a top view of a device according to the present invention.
Figure 2:
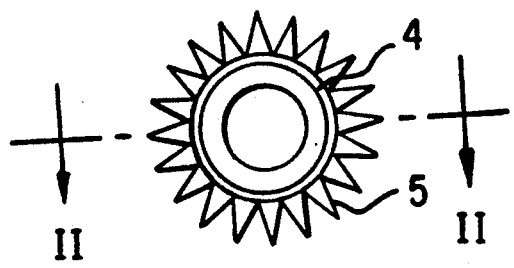
FIG. 2 shows a pin wheel.
Figure 2A:
FIG. 2A shows section II—II across the wheel shown in FIG. 2.

The device shown in the Figures comprises handle 1 having at the top fixed part 2, and movable part 3. Upon arcuate portions of parts 2 and 3 sits disposable wheel 4 around which are arranged pins 5. Movable part 3 is moved longitudinally by spring means 6 to hold the wheel 4. Knob 7 moves part 3 against the spring means to release wheel 4.

I claim:

1. A device for testing pin prick sensation comprising:
   a handle having an upper end;
   a detachable, rotatable wheel having a plurality of pins extending radially from the center of the wheel;
   movable holding means located at the upper end of the handle for holding the wheel on said upper end of the handle, said holding means providing an axis upon which the wheel rotates; and
   actuating means for moving the holding means such that the wheel is detached from the holding means whereby the wheel may be disposed of after said testing.

2. A device according to claim 1 wherein the holding means consists of a first part fixedly attached to the upper end of the handle and a second part which is movable in response to operation of the actuator means.

3. A device according to claim 2 wherein the actuator means includes a spring for biasing the second part of the holding means away from the first part of the holding means, whereby the wheel is held onto the upper end of the handle unless a force is applied against the spring whereby the second part of the holding means is moved toward the first part of the holding means.

4. A device according to claim 3 wherein the holding means includes a knob, said knob providing means for applying a force against the spring in order to move the second part of the holding means towards the first part of the holding means.

* * * * *